(12) United States Patent
Yao

(10) Patent No.: US 8,986,771 B2
(45) Date of Patent: Mar. 24, 2015

(54) DENDRITIC EMULSIFIERS AND METHODS FOR THEIR USE AND PREPARATION

(75) Inventor: Yuan Yao, West Lafayette, IN (US)

(73) Assignee: Purdue Research Institute Foundation, West Lafayette, IN (US)

( * ) Notice: Subject to any disclaimer, the term of this patent is extended or adjusted under 35 U.S.C. 154(b) by 149 days.

(21) Appl. No.: 13/509,868

(22) PCT Filed: Nov. 17, 2010

(86) PCT No.: PCT/US2010/057049
§ 371 (c)(1),
(2), (4) Date: Sep. 24, 2012

(87) PCT Pub. No.: WO2011/062999
PCT Pub. Date: May 26, 2011

(65) Prior Publication Data
US 2013/0017308 A1    Jan. 17, 2013

Related U.S. Application Data

(60) Provisional application No. 61/261,963, filed on Nov. 17, 2009.

(51) Int. Cl.
| | | |
|---|---|---|
| A61Q 19/00 | (2006.01) | |
| A23L 1/035 | (2006.01) | |
| A61K 8/06 | (2006.01) | |
| A61K 8/73 | (2006.01) | |
| B01F 17/00 | (2006.01) | |

(52) U.S. Cl.
CPC ............... *A61Q 19/00* (2013.01); *A23L 1/035* (2013.01); *A61K 8/062* (2013.01); *A61K 8/73* (2013.01); *A61K 2800/544* (2013.01); *B01F 17/0028* (2013.01)
USPC ........................................................ 426/602

(58) Field of Classification Search
None
See application file for complete search history.

(56) References Cited

U.S. PATENT DOCUMENTS

| | | | | | |
|---|---|---|---|---|---|
| 4,670,268 | A | * | 6/1987 | Mahmoud | 426/72 |
| 5,912,413 | A | * | 6/1999 | Myers et al. | 800/298 |
| 6,077,558 | A | * | 6/2000 | Euber | 426/601 |
| 6,451,362 | B1 | * | 9/2002 | Singh et al. | 426/93 |
| 6,995,300 | B2 | * | 2/2006 | Myers et al. | 800/284 |
| 8,178,323 | B2 | * | 5/2012 | De Vries et al. | 435/99 |
| 2008/0131941 | A1 | | 6/2008 | Kajiura et al. | |

OTHER PUBLICATIONS

Stecher, P. G. 1968. The Merck Index, 8th edition. Merck & Co., Inc. New Jersey. p. 501, 980.*
Bhosale, R. et al. 2007. Carbohydrate Polymers 68:447.*
Shogren, R. 2000. Starch/Starke 52:196.*
Song, X. 2006. Starch/Starke 58:109.*
Simonne, A. et al. 1996. Silver Queen May No Longer Be the Ruling Sweet Corn Variety. Highlights of Agricultural Research 43(2)1-3. Alabama Agricultural Experiment Station, Auburh, Alabama.*
Watson Stanley et al. 1987. Corn: Chemistry and Technology. American Association of Cereal Chemists, INc., St Paul, Minnesota. p. 260-262 & 433-435.*
Putaux, Jean-Luc et al. 1999. International Journal of Biological Macromolecules 26:145.*
Morris, J. et al 1939. J. Biol. Chem. 130:535.*
International Search Report for PCT/US2010/057049, mailed Aug. 2, 2011, 3pp.
International Preliminary Report on Patentability, mailed May 31, 2012, 5pp.
Liu et al., "Production of Octenyl Succinic Anhydride-Modified Waxy Corn Starch and Its Characterization", J. Agric. Food Chem., 2008, vol. 56, pp. 11499-11506.
Nakano et al., "Dispersion Stability of Phytoglycogen in Water/Phytoglycogen/Various Nonionic Surfactant Systems: Effect of Hydrophile—Lipophile Balance (HLB) of Nonionic Surfactants", Bull. Chem. Soc. Jpn., 1997, vol. 70, pp. 2943-2949.
Scheffler et al., "In Vitro Digestibility and Emulsification Properties of Phytoglycogen Octenyl Succinate", J. Agric. Food Chem., 2010, vol. 58, pp. 5140-5146.
Scheffler et al., "Phytoglycogen Octenyl Succinate, an Amphiphilic Carbohydrate Nanoparticle, and ε-Polylysine To Improve Lipid Oxidative Stability of Emulsions", J. Agric. Food Chem., 2010, vol. 58, pp. 660-667.

* cited by examiner

*Primary Examiner* — Carolyn Paden
(74) *Attorney, Agent, or Firm* — Brinks Gilson & Lione

(57) ABSTRACT

A dendritic emulsifier for forming an oil-in-water emulsion includes an anhydride-modified phytoglycogen or glycogen-type material. A method of preparing an oil-in-water emulsion includes: (a) combining oil, water, and a dendritic emulsifier; and (b) mixing a combination of the oil, water, and dendritic emulsifier. A method of preparing a dendritic emulsifier includes reacting an anhydride with a phytoglycogen or glycogen-type material in solution, thereby forming an anhydride-modified phytoglycogen or glycogen-type material.

18 Claims, 3 Drawing Sheets

DENDRITIC EMULSIFIERS AND METHODS FOR THEIR USE AND PREPARATION

RELATED APPLICATIONS

This application is a National Stage application of International Application No. PCT/US2010/057049 filed Nov. 17, 2010, which claims the benefit of U.S. Provisional Application No. 61/261,963, filed Nov. 17, 2009, the entire contents of which are hereby incorporated herein by reference.

TECHNICAL FIELD

The present teachings relate generally to the preparation and use of emulsifiers.

BACKGROUND

Emulsifiers are used in the food industry (and non-food industries) to form oil-in-water emulsions for the dispersion of hydrophobic components, such as nutrients (e.g., omega-3 fatty acids), flavors, regular lipids, and the like. Emulsifiers govern emulsion stability—a key factor in food quality—thereby protecting against coalescence (e.g., aggregation and creaming) and oxidation (which leads to rancidity and hazardous compounds).

Among the different types of emulsifiers, biopolymer-based emulsifiers typically exhibit a stronger capacity for emulsion stabilization than small molecule-based surfactants, forming a thick interfacial layer that allows for more effective steric repelling among oil droplets. If the biopolymer is charged, static repelling is also stronger for biopolymer-based interfacial layers. In addition, the migrations of oxidative compounds (e.g., oxygen, metal ions, and radicals) are greatly reduced due to the thick layer.

Gum arabic and starch octenyl succinate (starch-OSA) are two biopolymer-based emulsifiers that have been used in prior efforts to increase emulsion stability.

SUMMARY

The scope of the present invention is defined solely by the appended claims, and is not affected to any degree by the statements within this summary.

By way of introduction, a dendritic emulsifier for forming an oil-in-water emulsion includes an anhydride-modified phytoglycogen or glycogen-type material.

A method of preparing an oil-in-water emulsion includes (a) combining oil, water, and a dendritic emulsifier; and (b) mixing a combination of the oil, water, and dendritic emulsifier. The dendritic emulsifier includes an anhydride-modified phytoglycogen or glycogen-type material.

A method of preparing a dendritic emulsifier includes reacting an anhydride with a phytoglycogen or glycogen-type material in solution, thereby forming an anhydride-modified phytoglycogen or glycogen-type material. The anhydride is selected from the group consisting of succinic anhydride, octenyl succinic anhydride, and a combination thereof.

DETAILED DESCRIPTION

Modified phytoglycogen and glycogen-type materials with a strong capacity for stabilizing emulsions have been discovered and are described hereinbelow. The amphiphilic dendritic molecule phytoglycogen octenyl succinate (PG-OSA) has shown superior performance in forming and stabilizing oil-in-water emulsions. It was further discovered that PG-OSA has a much greater ability to stabilize emulsions than either starch octenyl succinate (starch-OSA) or gum arabic (GA). Moreover, in view of the abundant availability of phytoglycogen—which is a major carbohydrate in commercial sweet corn—PG-OSA has significant potential for industrial application. In addition, it is envisioned that large-scale production of glycogen can be readily achieved by industrial fermentation of yeast.

Throughout this description and in the appended claims, the following definitions are to be understood:

The term "dendritic" refers to a highly branched chemical structure.

The phrase "phytoglycogen or glycogen-type material" refers to dendritic (i.e., highly branched) α-D-glucan and carbohydrate nanoparticles. The term "phytoglycogen" generally refers to material that is derived from plants while the term "glycogen" generally refers to material that is derived from microbials and/or animals.

Figure 1:
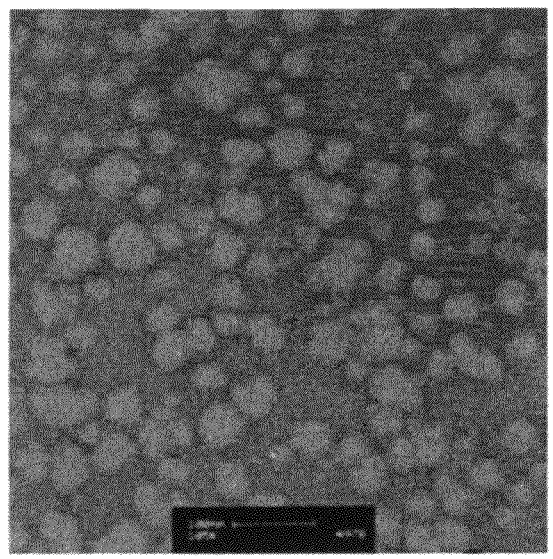
FIG. 1 shows a transmission electron microscopy (TEM) image of a phytoglycogen (scale bar=100 nm).

By way of introduction, phytoglycogen is a water-soluble glycogen-like α-D-glucan in plants. The largest source of phytoglycogen is the kernel of the maize mutant su1, a major genotype of sweet corn. The su1 mutation leads to a deficiency in SU1, an isoamylase-type starch debranching enzyme (DBE). In the biosynthesis of starch, starch synthase (SS), starch branching enzyme (SBE), and DBE work together to produce starch granules, with the primary role of DBE being to trim abnormal branches that inhibit the formation of starch crystals and granules. When there is a lack of DBE, the highly branched phytoglycogen is formed in the replacement of starch granules. FIG. 1 shows a TEM image of phytoglycogen nanoparticles with most particles ranging in size from 30 to 100 nm.

The highly branched structure of phytoglycogen results in its unusually high molecular density in dispersion. For example, in rice, the dispersed molecular density of phytoglycogen is over 10 times that of starch. Similarly, the molecular density of phytoglycogen from maize is around 1000 g/mol/$nm^3$ as compared to about 50 g/mol/$nm^3$ for amylopectin. The high density of phytoglycogen provides structural integrity and allows for dense grafting of functional groups.

Each phytoglycogen particle contains hundreds or thousands of glucan chains forming a highly packed structure. Without wishing to be bound by a particular theory or to in any way limit the scope of the appended claims or their equivalents, it is presently believed that that the spherical phytoglycogen particle grows from the non-reducing ends on the surface by periodic branching and elongation of chains. In phytoglycogen, there is no long chain that connects individual clusters as in the case of an amylopectin molecule, which suggests a fundamental structural difference between phytoglycogen and amylopectin.

Figure 2:
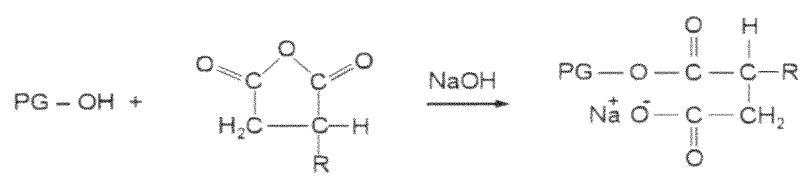
FIG. 2 shows a representative chemical scheme for the reaction of phytoglycogen (PG-OH) with an anhydride reagent.

FIG. 2 shows a representative synthetic scheme for modifying a phytoglycogen in accordance with the present teachings. Among food-grade starch-related reactions, succinylation and octenyl succinylation (both allowed by the U.S. Food and Drug Administration for food applications) have been used to introduce negative charge and/or hydrophobicity. The scheme shown in FIG. 2 can be readily modified to achieve both succinylation and octenyl succinylation: when R is hydrogen, the anhydride reagent is succinic anhydride; when R is —CH=CH—(CH$_2$)$_5$—CH$_3$, the anhydride reagent is octenyl succinic anhydride. The surface properties of a modified phytoglycogen can be controlled by the degree of substitution (DS).

In accordance with the present teachings, the amphiphilic dendritic molecule PG-OSA shows superior performance in forming and stabilizing oil-in-water emulsions. In oil-in-water emulsions, the nature of the amphiphilic interfacial layer governs physical stability to environmental stresses, chemical stability to oxidation, and the release pattern of encapsulated lipophilic compounds. Without wishing to be bound by a particular theory or to in any way limit the scope of the appended claims or their equivalents, it is presently believed that the advantages of biopolymer-based emulsifiers—such as waxy starch octenyl succinate (WX-OSA) and gum arabic (both of which are used in the industry)—involve their capability of forming a thick interfacial layer that maintains the physical stability of the emulsion through steric repelling among individual oil droplets.

Recently, multilayer constructs (FIG. 3, bottom right) have been developed using emulsifiers and biopolymers (laminated layers formed by electrostatic attraction) with an aim of tailoring the thickness and permeability of interfacial layers. However, the formation of stable multilayer emulsions requires careful control over system composition and preparation procedures in order to avoid droplet aggregation. Thus, at present, it is only possible to prepare dilute emulsions due to bridging flocculation.

Figure 3:
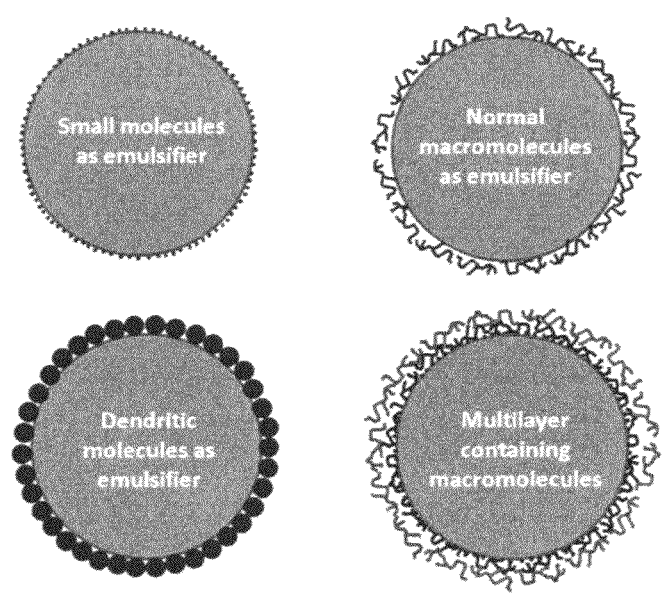
FIG. 3 shows an illustration of interfacial layers over oil droplets in various oil-in-water emulsions, wherein the layers are formed by small molecules (upper left), macromolecules (upper right), multilayer (bottom right), and dendritic molecules (bottom left).

The illustration at the bottom left of FIG. 3 depicts a nanolayer of PG-OSA dendritic molecules at an oil-in-water interface. Compared with small molecule emulsifiers (FIG. 3, upper left), the PG-OSA particles provide superior steric hindrance to droplet coalescence or aggregation. Moreover, as compared to regular amphiphilic macromolecules (e.g., WX-OSA or GA), the interfacial layer formed by dendritic particles is denser and structurally more defined. Finally, as compared to a multilayer interfacial structure (FIG. 3, bottom right), the interfacial layer formed by dendritic particles avoids the problem of bridging flocculation due to the simplicity of formation of the nano-layer. In addition, the interfacial layer formed by dendritic particles has the added benefit of having a high layer density (and, therefore, a low permeability to oxidative compounds).

The following examples and representative procedures illustrate features in accordance with the present teachings, and are provided solely by way of illustration. They are not intended to limit the scope of the appended claims or their equivalents.

Materials and Methods

Phytoglycogen is extracted from the matured kernels of an su1-containing sweet corn cultivar, Silver Queen. To isolate native phytoglycogen, the kernels of sweet corn are ground, soaked in deionized water, and homogenized. The non-soluble materials (e.g., fiber, starch, protein, oil) are removed using repetitive filtration and centrifugation. Phytoglycogen is precipitated from the supernatant by adding 3 volumes of alcohol, which can effectively remove small, soluble molecules. The precipitate is collected by filtration and dehydrated using anhydrous alcohol and acetone. The phytoglycogen thus obtained is rather pure with a low soluble protein content. The yield of phytoglycogen ranges from 20 to 25% of dry kernels.

For the modification of phytoglycogen, a solution of phytoglycogen derivative (5% w/w) is adjusted to pH 8.5 followed by the addition of octenyl succinic anhydride (OSA) at 25° C. During the reaction, pH is maintained between 8.5 and 9.0. To conclude the reaction, the solution is adjusted to pH 6.5 followed by the addition of 3 volumes of ethanol. The precipitate undergoes repetitive dispersion-centrifugation washing using 80% ethanol, and is then dehydrated by anhydrous ethanol and acetone. The degree of substitution (DS), which is the molar ratio between substitution groups and glucosyl units, is determined by the titration of carboxyl group of octenyl succinate (JECFA method CXAS/1991). Briefly, PG-OSA is fully acidified using 2.5 N HCl and then treated by repetitive dispersion-centrifugation washing using 90% isopropanol to remove free HCl. A solution of AgNO$_3$ (0.1 N) is used to test for the presence of chloride to ensure a complete removal of HCl. After the complete removal of HCl, a solution of 0.01 N NaOH is used to determine the amount of H$^+$ (which is equal to the molar amount of grafted octenyl succinate groups). Typically, the efficiency of substitution (i.e., the molar yield of grafted groups) ranges from 30 to 70%. By controlling the amount of added OSA, the DS value distributes in the range of 0.002 to 0.20.

To prepare an emulsion (e.g., for fish oil), fish oil 5% and PG-OSA 10% (w/w based on water) are mixed with deionized water, treated with a high-speed mixer (IKA T25) at 20,000 rpm for 2 minutes, and homogenized at room temperature using a high pressure homogenizer (Nano DeBee, Bee International) at 25,000 psi. To track the susceptibility of the emulsion to coalescence during storage, immediately after homogenization and after 4 weeks at 4° C. storage, the emulsion is diluted by 125 times and the particle size distribution is measured using a Zetasizer Nano ZS-90 (Malvern). To evaluate lipid oxidation at different storage times, the ability of peroxides (produced by lipid oxidation) to oxidize ferrous ions to ferric ions was measured. Briefly, an aliquot of emulsion is added to isooctane-2-propanol, followed by lipid extraction using vortex and centrifugation. The lipid extraction is added with a mixture of methanol and butanol, ammonium thiocyanate, and ferrous iron acid solution. After incubation, the absorbance is measured at 510 nm against standard ferric ions curve and used to denote the extent of lipid oxidation.

Figure 4A:
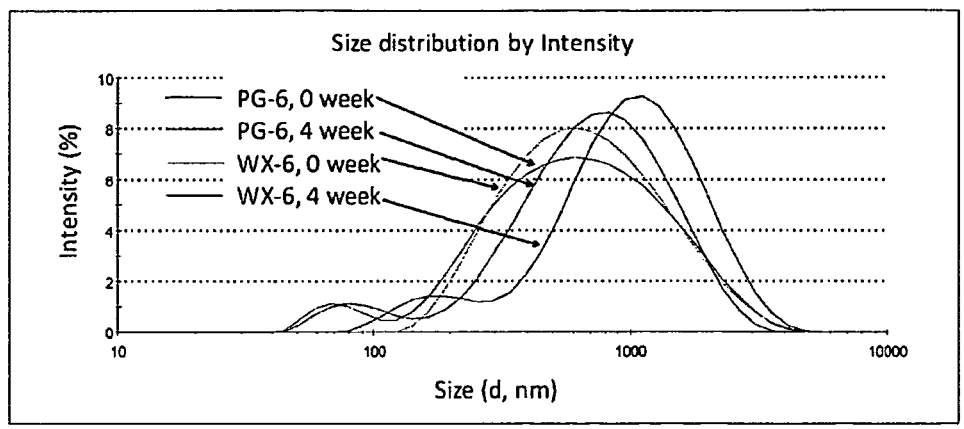
FIGS. 4a and 4b show graphs of intensity vs. particle size distribution for oil-in-water emulsions at different stages.
Figure 4B:
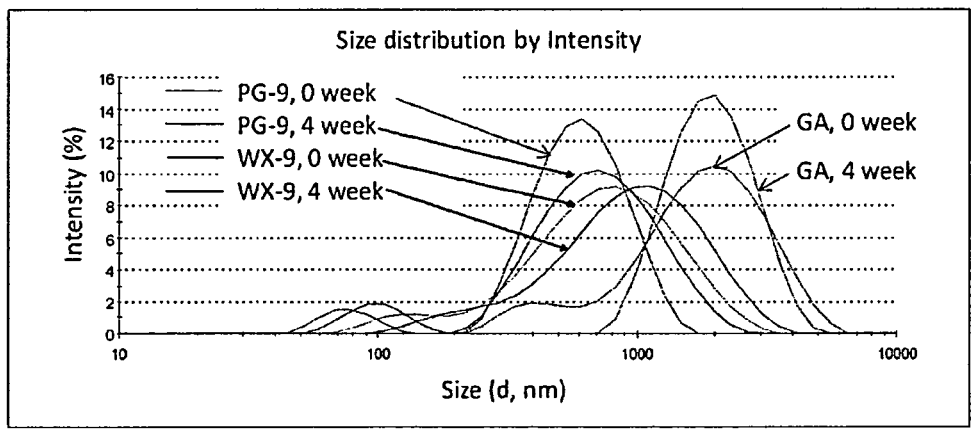

FIGS. 4a and 4b show plots of intensity vs. size for the formation and stability of fish oil emulsions emulsified by phytoglycogen octenyl succinate (PG-6 and PG-9), waxy corn starch octenyl succinate (WX-6 and WX-9), and gum arabic (GA). In accordance with the present teachings, it was discovered that PG-OSA offers a greater capability to stabilize oil-in-water emulsions than either WX-OSA or GA. Thus, the particle size of oil droplets over a 4-week storage period is more stable with PG-OSA than with either WX-OSA or GA.

The degree of octenyl succinylation is comparable between PG-6 and WX-6 (0.023 and 0.026 respectively) (FIG. 4a) and between PG-9 and WX-9 (0.050 and 0.043 respectively) (FIG. 4b). The particle size distribution was measured immediately after homogenization (0 week) and after the 4-week storage at 4° C. Evidently, the droplet particle size of a PG-6 or PG-9 emulsion is much more stable than that of WX-6 or WX-9. Both PG-OSA and WX-OSA performed substantially better than GA in forming emulsion.

Table 1 shows data for the relative levels of peroxide produced due to oxidation of the fish oil after storage for around 10 weeks. Evidently, the oxidation of fish oil in emulsion was much lower for PG-6 and PG-9 than for WX-6, WX-9, and gum arabic.

TABLE 1

Relative level of peroxide produced using PG-OSA, WX-OSA, and GA

| | Emulsifier | | | | |
|---|---|---|---|---|---|
| | PG-6 | PG-9 | WX-6 | WX-9 | Gum Arabic |
| Relative level of peroxide | 0.448 | 0.533 | 0.894 | 0.936 | 0.935 |

The following literature provides information that may be useful in accordance with the present teachings and each document is hereby incorporated by reference in its entirety, except that in the event of any inconsistent disclosure or definition from the present specification, the disclosure or definition herein shall be deemed to prevail: (1) Guzey, D., McClements, D. J. "Impact of electrostatic interactions on formation and stability of emulsions containing oil droplets coated by beta-lactoglobulin-pectin complexes," *Journal of Agricultural and Food Chemistry*, 2007, 55, 475-485; (2) James, M. G., Robertson, D. S., Myers, A. M., "Characterization of the maize gene sugary1, a determinant of starch composition in kernels," *Plant Cell*, 1995, 7, 417-429; (3) Klinkesorn, U., Sophanodora, P., Chinachoti, P., Decker, E. A., McClements, D. J. "Encapsulation of emulsified tuna oil in two-layered interfacial membranes prepared using electrostatic layer-by-layer deposition," *Food Hydrocolloids*, 2005, 19, 1044-1053; (4) McClements, D. J., Decker, E. A., Weiss, J. "Emulsion-based delivery systems for lipophilic bioactive components," *Journal of Food Science*, 2007, 72, R109-R124; (5) Myers, A. M., Morell, M. K., James, M. G., Ball, S. G. "Recent progress toward understanding the amylopectin crystal," *Plant Physiology*, 2000, 122, 989-997; (6) Nakamura, Y. "Towards a better understanding of the metabolic system for amylopectin biosynthesis in plants: Rice endosperm as a model tissue," *Plant and Cell Physiology*, 2002, 43, 718-725; (7) Ogawa, S., Decker, E. A., McClements, D. J. "Influence of environmental conditions on the stability of oil in water emulsions containing droplets stabilized by lecithin-chitosan membranes," *Journal of Agricultural and Food Chemistry*, 2003, 51, 5522-5527; (8) Shantha, N. C., Decker, E. A. "Rapid, sensitive, iron-based spectrophotometric methods for determination of peroxide values of food lipids," *Journal of AOAC International*, 1994, 77, 421-424; (9) Shin, J., Simsek, S., Reuhs, B., Yao, Y. "Glucose release of water-soluble starch-related a-glucans by pancreatin and amyloglucosidase is affected by the abundance of a-1,6 glucosidic linkages," *Journal of Agricultural and Food Chemistry*, 2008, 56, 10879-10886; (10) Thompson, D. B. "On the non-random nature of amylopectin branching," *Carbohydrate Polymer*, 2000, 43, 223-239; (11) Wong, K., Kubo, A., Jane, J., Harada, K., Satoh, H., Nakamura, Y. "Structures and properties of amylopectin and phytoglycogen in the endosperm of sugary-1 mutants of rice," *Journal of Cereal Science*, 2003, 37, 139-149; (12) Wurzburg, O. B. "Modified Starch," in *Food Polysaccharides and Their Applications, Second Edition*, edited by Stephen, A. M., Phillips, G. O., and Williams, P. A., CRC, 2006; and (13) Yao, Y. "Biosynthesis of starch," in *Comprehensive Glycoscience*, edited by Hans Kamerling, Elsevier, 2007.

The foregoing detailed description and accompanying drawings have been provided by way of explanation and illustration, and are not intended to limit the scope of the appended claims. Many variations in the presently teachings will be apparent to one of ordinary skill in the art, and remain within the scope of the appended claims and their equivalents.

The invention claimed is:

1. A dendritic emulsifier for forming an oil-in-water emulsion comprising an anhydride-modified, water-soluble phytoglycogen or water-soluble glycogen-type material.

2. The emulsifier of claim 1 wherein the anhydride comprises succinic anhydride.

3. The emulsifier of claim 1 wherein the anhydride comprises octenyl succinic anhydride.

4. The emulsifier of claim 1 wherein the dendritic emulsifier comprises phytoglycogen octenyl succinate.

5. The emulsifier of claim 4 wherein a degree of substitution of the phytoglycogen octenyl succinate is between 0.002 and 0.20.

6. A method of preparing an oil-in-water emulsion comprising: combining oil, water, and a dendritic emulsifier; and mixing a combination of the oil, water, and dendritic emulsifier; wherein the dendritic emulsifier comprises an anhydride-modified, water-soluble phytoglycogen or water-soluble glycogen-type material.

7. The method of claim 6 further comprising homogenizing the combination of the oil, water, and dendritic emulsifier.

8. The method of claim 6 wherein the anhydride comprises succinic anhydride.

9. The method of claim 6 wherein the anhydride comprises octenyl succinic anhydride.

10. The method of claim 6 wherein the dendritic emulsifier comprises phytoglycogen octenyl succinate.

11. The method of claim 6 wherein the oil-in-water emulsion exhibits lower relative levels of peroxide after 10 weeks as compared to the relative levels of peroxide after 10 weeks in the same emulsion prepared using a starch octenyl succinate emulsifier instead of the dendritic emulsifier.

12. The method of claim 6 wherein the oil-in-water emulsion exhibits lower relative levels of peroxide after 10 weeks as compared to the relative levels of peroxide in the same emulsion prepared using a gum arabic emulsifier instead of the dendritic emulsifier.

13. The method of claim 6 wherein the oil-in-water emulsion exhibits decreased droplet coalescence or aggregation relative to the droplet coalescence or aggregation of the same emulsion prepared using a starch octenyl succinate emulsifier instead of the dendritic emulsifier.

14. The method of claim 6 wherein the oil-in-water emulsion exhibits decreased droplet coalescence or aggregation relative to the droplet coalescence or aggregation of the same emulsion prepared using a gum arabic emulsifier instead of the dendritic emulsifier.

15. The method of claim 6 wherein the oil-in-water emulsion exhibits decreased susceptibility to oxidation relative to the susceptibility to oxidation of the same emulsion prepared using a starch octenyl succinate emulsifier instead of the dendritic emulsifier.

16. The method of claim 6 wherein the oil-in-water emulsion exhibits decreased susceptibility to oxidation relative to the susceptibility to oxidation of the same emulsion prepared using a gum arabic emulsifier instead of the dendritic emulsifier.

17. A method of preparing a dendritic emulsifier comprising: reacting an anhydride with a water-soluble phytoglycogen or water-soluble glycogen-type material in solution, thereby forming an anhydride-modified phytoglycogen or glycogen-type material; wherein the anhydride is selected from the group consisting of succinic anhydride, octenyl succinic anhydride, and a combination thereof.

18. The method of claim 17 wherein the anhydride comprises octenyl succinic anhydride and wherein the dendritic emulsifier comprises phytoglycogen octenyl succinate.

* * * * *

UNITED STATES PATENT AND TRADEMARK OFFICE
CERTIFICATE OF CORRECTION

| | | |
|---|---|---|
| PATENT NO. | : 8,986,771 B2 | Page 1 of 1 |
| APPLICATION NO. | : 13/509868 | |
| DATED | : March 24, 2015 | |
| INVENTOR(S) | : Yuan Yao | |

It is certified that error appears in the above-identified patent and that said Letters Patent is hereby corrected as shown below:

<u>On the Title Page</u>

(73) Assignee: After "Purdue Research" and before "Foundation" delete "Institute"

Signed and Sealed this
Twenty-second Day of March, 2016

Michelle K. Lee
*Director of the United States Patent and Trademark Office*